(12) United States Patent
Nett et al.

(10) Patent No.: US 11,432,783 B2
(45) Date of Patent: Sep. 6, 2022

(54) METHODS AND SYSTEMS FOR BEAM ATTENUATION

(71) Applicant: GE Precision Healthcare LLC, Milwaukee, WI (US)

(72) Inventors: Brian Edward Nett, Wauwatosa, WI (US); Chelsey Lewis, Waukesha, WI (US); Bradley Gabrielse, Brookfield, WI (US); Karen Procknow, Willowbrook, IL (US); Holly McDaniel, Waukesha, WI (US); Meghan Lynn Yue, Johnson Creek, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 321 days.

(21) Appl. No.: 16/740,041

(22) Filed: Jan. 10, 2020

(65) Prior Publication Data
US 2021/0212642 A1 Jul. 15, 2021

(51) Int. Cl.
*A61B 6/03* (2006.01)
*A61B 6/06* (2006.01)
*A61B 6/04* (2006.01)
*G06T 7/00* (2017.01)
*A61B 6/00* (2006.01)

(52) U.S. Cl.
CPC ............ *A61B 6/4035* (2013.01); *A61B 6/032* (2013.01); *A61B 6/04* (2013.01); *A61B 6/06* (2013.01); *A61B 6/5205* (2013.01); *G06T 7/0012* (2013.01); *G06T 2207/10024* (2013.01); *G06T 2207/10081* (2013.01); *G06T 2207/20024* (2013.01); *G06T 2207/30004* (2013.01); *G06T 2207/30168* (2013.01)

(58) Field of Classification Search
CPC .. A61B 6/032; A61B 6/04; A61B 6/06; A61B 6/4035; A61B 6/461; A61B 6/488; A61B 6/5205; A61B 6/545; G06T 7/0012; G06T 2207/10024; G06T 2207/10081; G06T 2207/20024; G06T 2207/30004; G06T 2207/30168
See application file for complete search history.

(56) References Cited

U.S. PATENT DOCUMENTS

| 8,942,341 B2 | 1/2015 | Hsieh et al. |
| 10,082,473 B2 | 9/2018 | Pack et al. |
| 2010/0310049 A1* | 12/2010 | Sipiorski ............... A61B 6/488 378/98.7 |

OTHER PUBLICATIONS

"The importance of patient centering on CT radiation dose optimization," Philips Healthcare Website, Available Online at https://www.usa.philips.com/c-dam/b2bhc/master/clinical-solutions/dosewise-solution-page/TheimportanceofpatientcenteringonCTradiationdoseoptimization.pdf, Available as Early as Jan. 1, 2016, 2 pages.

* cited by examiner

*Primary Examiner* — Mark R Gaworecki
(74) *Attorney, Agent, or Firm* — McCoy Russell LLP

(57) ABSTRACT

Various methods and systems are provided for displaying to an operator an attenuation map of a filter relative to a current location of an anatomical feature of a subject; and in response to the anatomical feature being within a region of the attenuation map, prompting an operator to reposition the subject. In this way, centering of the anatomical feature relative to an attenuation system may be facilitated for improved image quality.

19 Claims, 8 Drawing Sheets

METHODS AND SYSTEMS FOR BEAM ATTENUATION

FIELD

Embodiments of the subject matter disclosed herein relate to diagnostic medical imaging, and more particularly, to computed tomography imaging setup with an x-ray beam attenuation system such as a bowtie filter.

BACKGROUND

Noninvasive imaging modalities may transmit energy in the form of radiation into an imaging subject. Based on the transmitted energy, images may be subsequently generated indicative of the structural or functional information internal to the imaging subject. In computed tomography (CT) imaging, radiation transmits from a radiation source to a detector through the imaging subject. An attenuation system such as a bowtie filter may be positioned between the radiation source and the imaging subject for adjusting the spatial distribution of the radiation energy based on the anatomy of the imaging subject.

The bowtie filter may be designed to distribute higher radiation energy to specific imaging region of the subject. As a result, the amplitude of signal received by the imaging detector is improved, and the radiation dose on the periphery of the specific imaging subject is reduced. The x-ray beam passing through a portion of the bowtie filter may be attenuated with the attenuation increasing gradually towards the edge of the filter. As an example, the beam passing through the center of the filter may not be attenuated while attenuation at the edges of the filter may be highest. Different anatomy of the subject may require different bowtie filters. For example, bowtie filters of different shape and size may be designed to image distinct regions of the subject's body such as the head, the chest, and the abdomen.

BRIEF DESCRIPTION

In one embodiment, a method for an imaging system, comprises displaying a representation of an attenuation map of a filter relative to a current location of an anatomical feature of a subject, and in response to the anatomical feature being within a region of the representation of the attenuation map, prompting an operator to reposition the subject. In this way, a representation of an attenuation map relative to an anatomical feature may be used to adjust the position of the subject for improved imaging.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
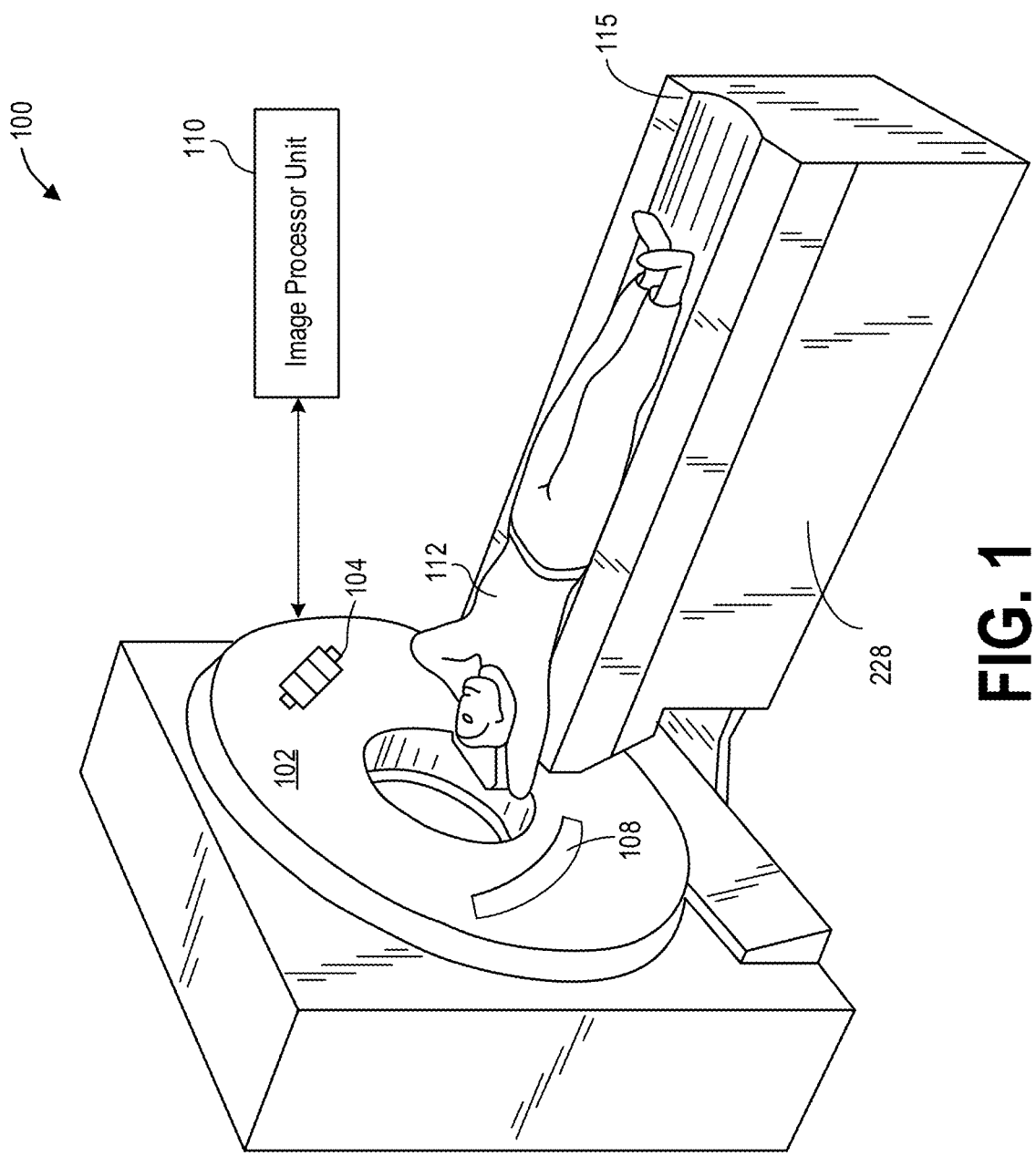
FIG. 1 shows a pictorial view of an imaging system according to an embodiment of the invention.
Figure 2:
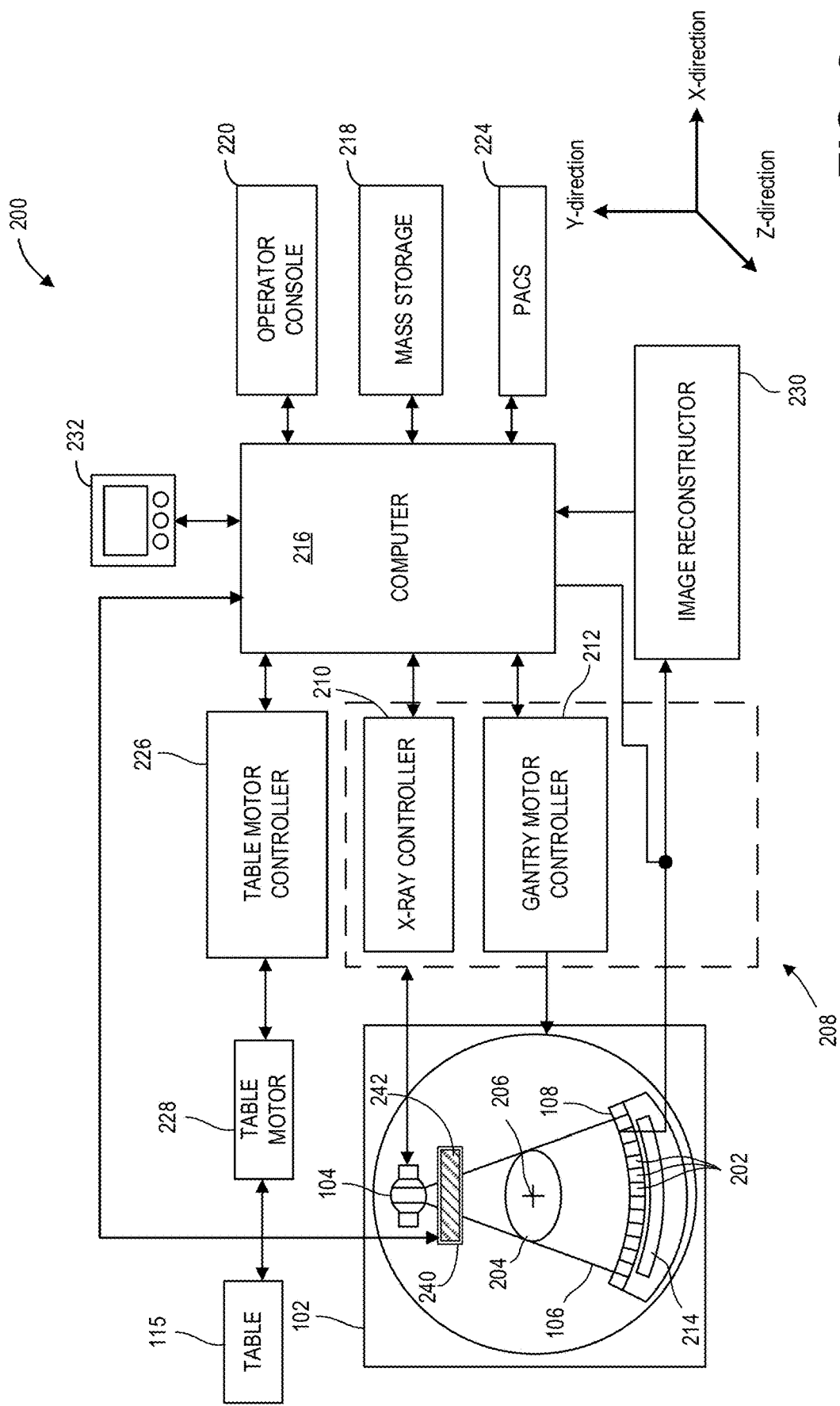
FIG. 2 shows a block schematic diagram of an exemplary imaging system according to an embodiment of the invention.
Figure 4B:
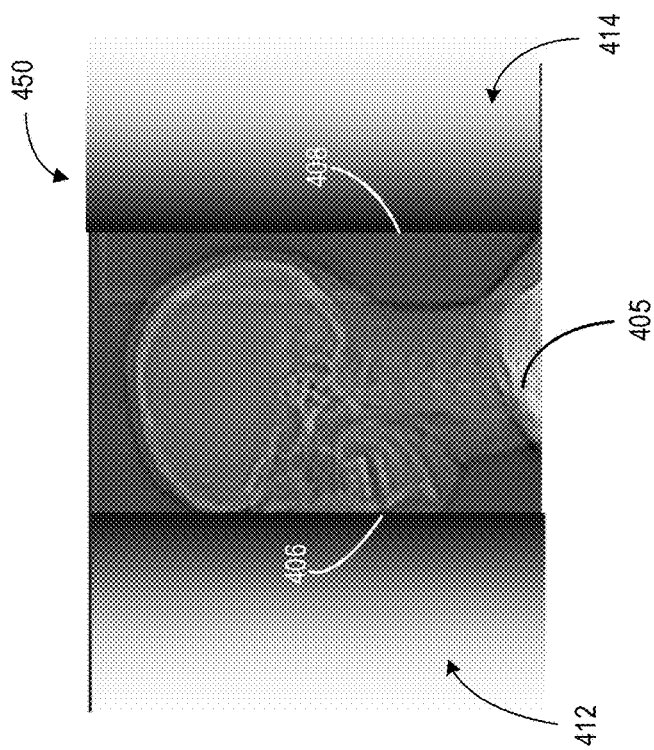
FIG. 4B shows a second example positioning of the subject shown in the scout scan image relative to the representation of the attenuation map corresponding to the bowtie filter.
Figure 4A:
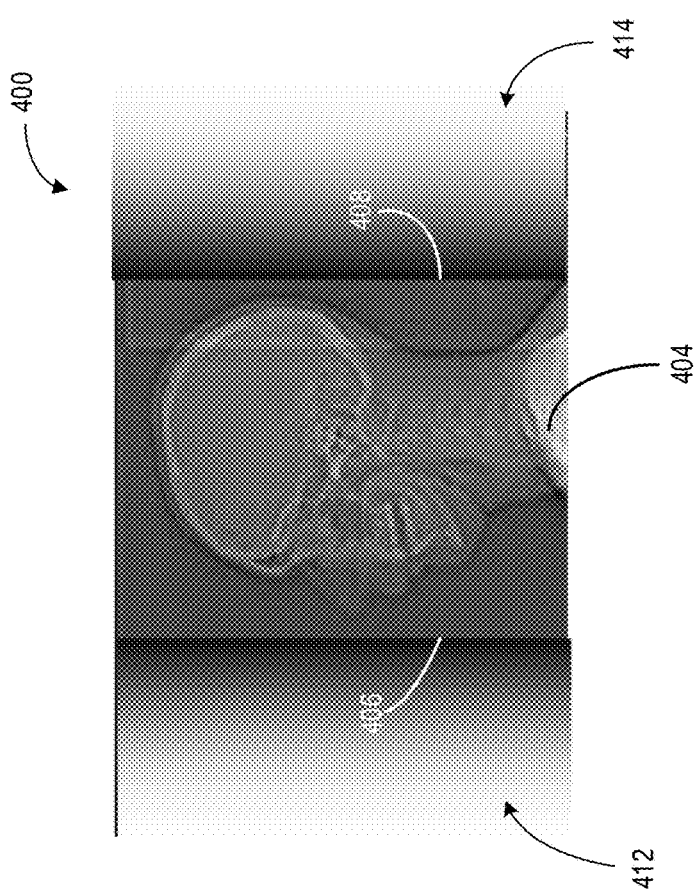
FIG. 4A shows a first example positioning of a subject shown in a scout scan image relative to an representation of an attenuation map corresponding to a bowtie filter.
Figure 4C:
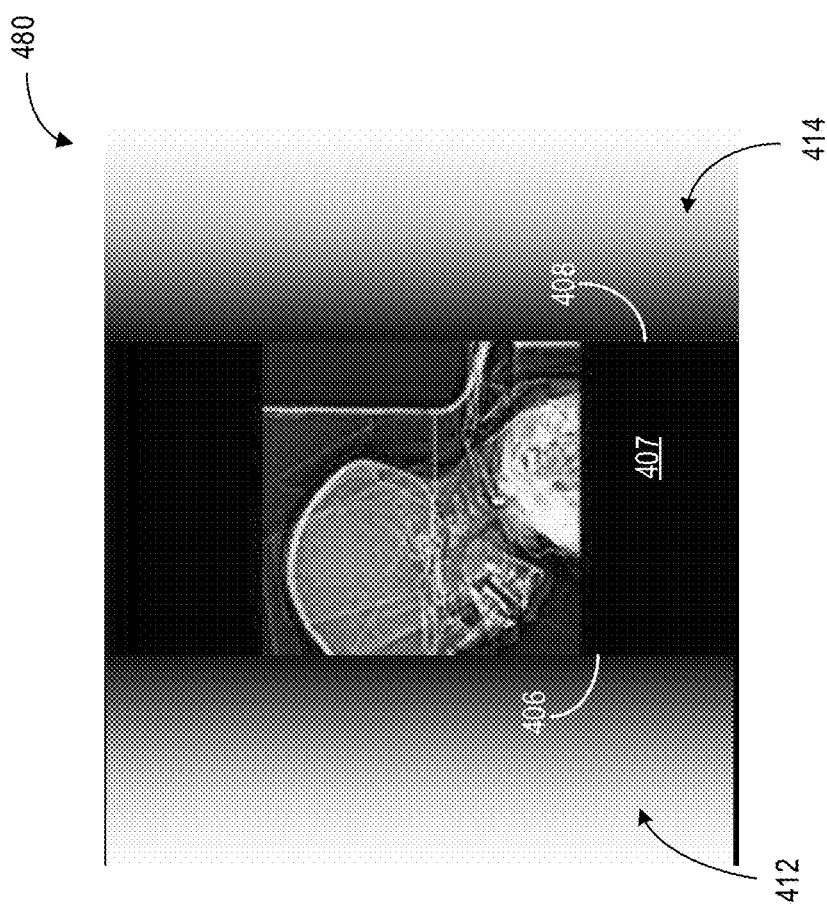
FIG. 4C shows a third example positioning of the subject relative to the representation of the attenuation map corresponding to the bowtie filter.
Figure 5B:
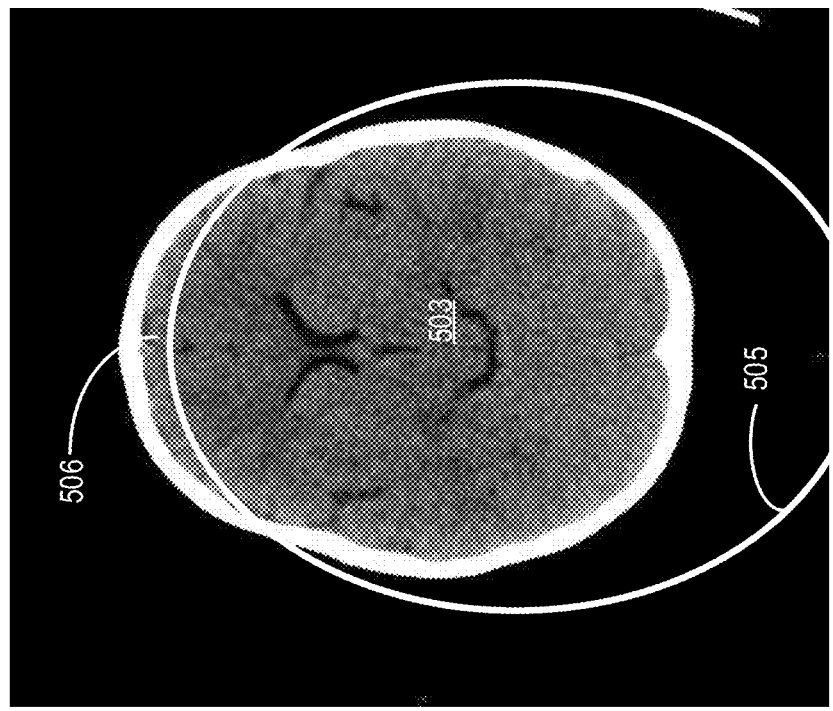
FIG. 5B shows a second example positioning of the bowtie filter attenuation region relative to another position to an anatomical feature.
Figure 5A:
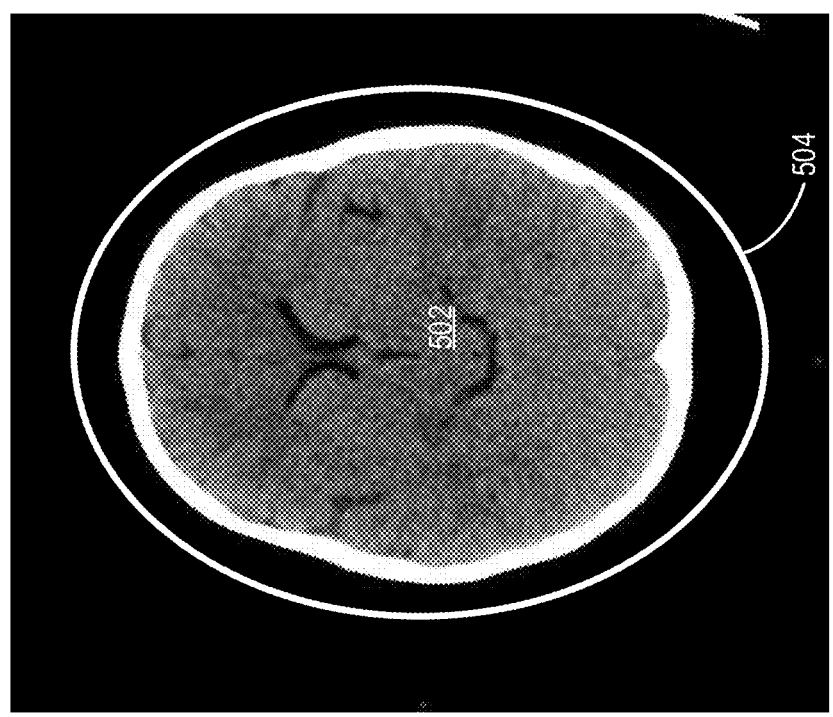
FIG. 5A shows a first example positioning of a bowtie filter attenuation region relative to a current position to an anatomical feature.
Figure 6B:
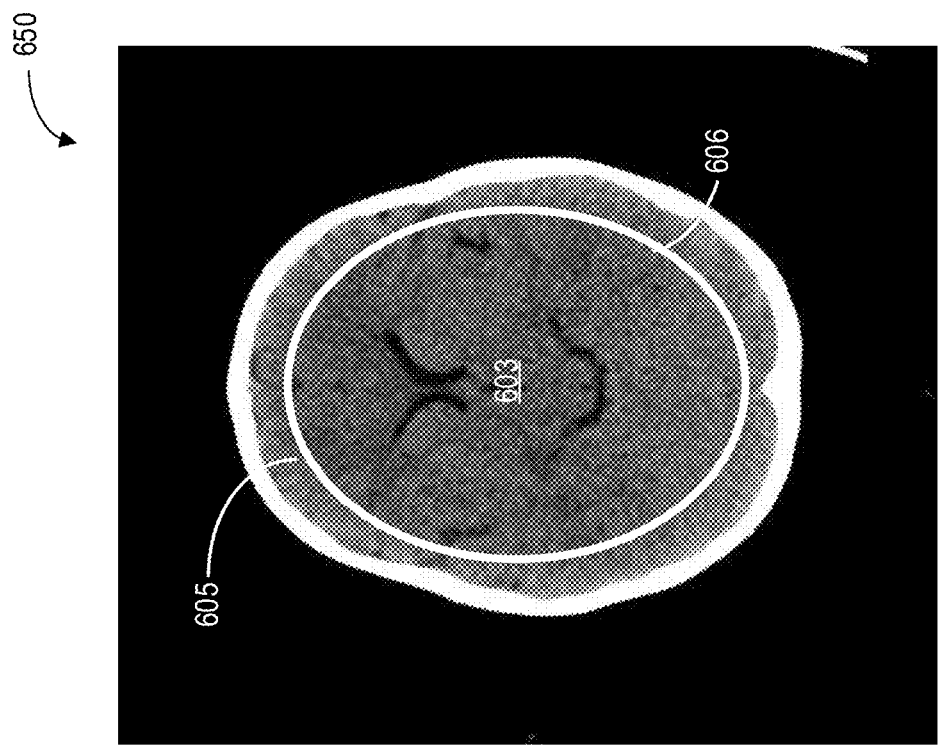
FIG. 6B shows an attenuation region of a second bowtie filter relative to a current position to an anatomical feature.
Figure 6A:
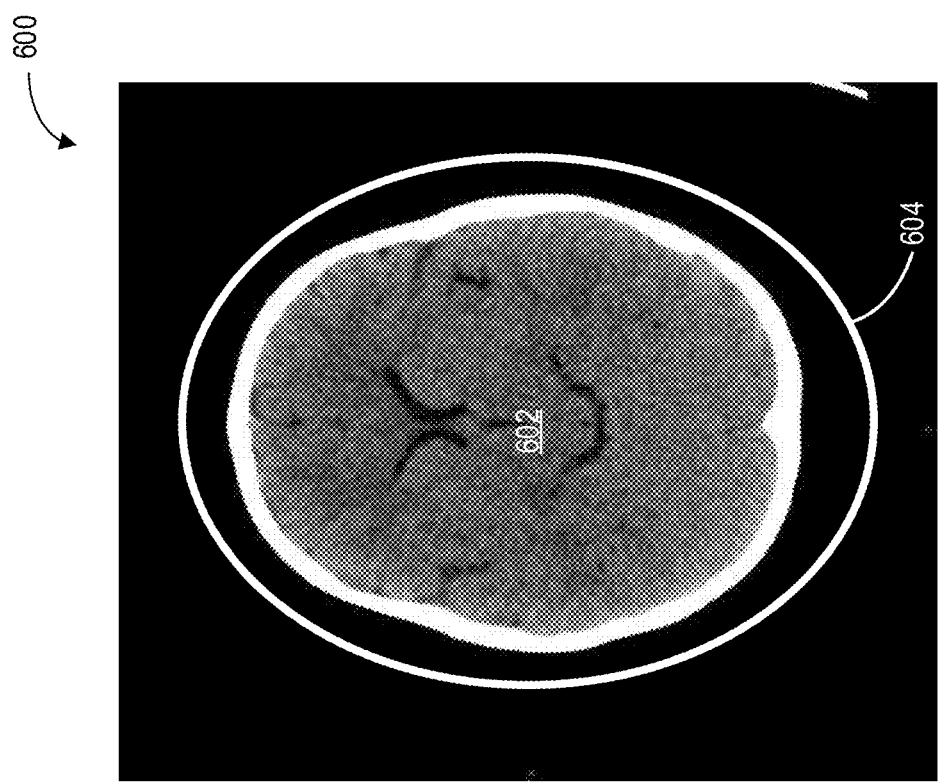
FIG. 6A shows an attenuation region of a first bowtie filter relative to a current position to an anatomical feature.

The following description relates to various embodiments of x-ray imaging of a subject. In particular, systems and methods are provided for CT imaging using an attenuation system such as a bowtie filter. FIGS. 1-2 show an example embodiment of an imaging system, wherein the one or more filters are positioned between the radiation source and the imaging subject. Different filters may be selected based on the anatomy of the imaging subject being imaged. The subject may be centered with respect to the center of the selected filter to attain a desired scan field of view. FIG. 2 shows an example view of a bowtie filter used for attenuation of an x-ray beam reaching a detector via a subject that is scanned. Representations of attenuation maps of a bowtie filter overlaid on scout scan images showing different positions of the subject is shown in FIGS. 4A-4C. Beam attenuation in a bowtie filter may start from a boundary of an attenuation region on the bowtie filter and extend towards the edges (away from the center of the filter) with little or no beam attenuation close to the center of the filter and the region outside the attenuation region. FIGS. 5A-5B show location of an attenuation region of a bowtie filter relative to different positions of an anatomical feature of the subject. The attenuation region of the bowtie filter is dependent on a size of the bowtie filter. FIGS. 6A-6B show attenuation regions of two bowtie filters relative to a current position to an anatomical feature. Based on an overlay of a representation of the attenuation map of a bowtie filter with an image of an anatomical feature to be scanned, as shown in the example method of FIG. 7, a subject may be positioned.

Though a CT imaging system is described by way of example, it should be understood that the present techniques may also be useful when applied to images acquired using other imaging systems, such as x-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging system is provided merely as an example of one suitable imaging system.

Various embodiments may be implemented in connection with different types of imaging systems. For example, various embodiments may be implemented in connection with a CT imaging system in which a radiation source projects a fan- or cone-shaped beam that is collimated to lie within an x-y plane of a Cartesian coordinate system and generally referred to as an "imaging plane." The x-ray beam passes through an imaging subject, such as a patient. The beam, after being attenuated by the imaging subject, impinges upon an array of radiation detectors. The intensity of the attenuated radiation beam received at the detector array is dependent upon the attenuation of an x-ray beam by the imaging subject. Each detector element of the array produces a separate electrical signal that is a measurement of the beam intensity at the detector location. The intensity measurements from all the detectors are acquired separately to produce a transmission profile.

In third-generation CT imaging systems, the radiation source and the detector array are rotated with a gantry within the imaging plane and around an object (such as a region of the subject) to be imaged such that the angle at which the x-ray beam intersects the imaging subject constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial diagnostic scan, the projection data is processed to construct an image that corresponds to a two-dimensional slice taken through the imaging subject. A scout scan (also referred herein as localizer scan) provides a projection view along a longitudinal axis of the imaging subject and generally provides aggregations each including internal structures of the subject. One method for reconstructing an image from a set of projection data is referred to in the art as a filtered back projection technique. This process converts the attenuation measurements from a scan into integers called "CT numbers" or "Hounsfield units" (HU), which are used to control the brightness of a corresponding pixel on a display.

A bowtie filter is typically used to selectively attenuate a portion of the x-ray beam reaching a detector of a CT imaging system after passing through a subject. By attenuating a portion of the beam that does not pass through an anatomy of interest (in the subject), radiation exposure of the subject and any other person present in the room may be reduced. As the beam passes through the anatomy of interest, a portion of the beam may be absorbed by the subject and the beam exiting the subject may be attenuated. Therefore, by attenuating the portion of the beam that does not pass through an anatomy of interest via a bowtie filter, the flux of x-ray received at a detector may be maintained at a uniform level.

In one example, the beam passing through the center of the bowtie filter may not be significantly attenuated (such as less than 5% attenuation of the flux) and significant attenuation (such as at least 5% of the flux) of the beam may start from a certain point (also referred herein as attenuation boundary) on the bowtie filter and extend to the edge of the filter (away from the center). The degree of attenuation of the beam may gradually increase from the attenuation boundary to the edge of the bowtie filter. Therefore, an x-ray beam passing through the bowtie filter outside the attenuation boundary (towards the edge of the filter) on either side from the center of filter may be gradually attenuated. Also, the position of the attenuation boundary of a bowtie may be based on a size of the bowtie such that for a smaller bowtie filter, the attenuation boundary of the bowtie may be near (or at) the center of the filter while the attenuation boundary of a larger bowtie filter may be further away from the center of the filter.

However, if an anatomy of interest (to be scanned during a diagnostic scan) is off centered relative to the center of the bowtie filter selected to be used during the scanning, a part of the x-ray beam reaching the anatomy of interest may be attenuated. Also, if a smaller bowtie filter is erroneously selected for use during scanning of the anatomy of interest, a part of the x-ray beam reaching the anatomy of interest may be attenuated. Use of an attenuated beam for imaging may result in a reduction of image quality.

In order to align the subject with the center of a selected bowtie filter, a representation of an attenuation map of the bowtie filter may be overlaid with an image of the anatomy of interest. In one example, the representation of the attenuation map may be an attenuation map. The image of the anatomy of interest may be obtained from a scout scan preceding the diagnostic scan or an immediately previous diagnostic scan performed in a series of scans. A representation of the attenuation map may show the attenuation boundary on the image corresponding to the attenuation boundary on the bowtie filter from where the attenuation region begins. Any part of the image outside the attenuation boundary (towards the edge of the bowtie filter) may be scanned using attenuated beam. In other words, a part of the subject's anatomy corresponding to the region outside the attenuation boundary may receive attenuated x-ray beam. A degree of attenuation may gradually increase towards the edge of the bowtie filter. A representation of the attenuation map corresponding to each bowtie filter may be calibrated and saved in the memory of the CT device. A visualization of the image of the anatomy of interest overlaid with the representation of the attenuation map showing the attenuation boundary and the graduated change in attenuation over the portion of the image outside the attenuation boundary may be available to an operator. Also, in response to the anatomy of interest not being aligned with the center of the bowtie filter (odd-centered), the operator may be prompted to align the subject and center the anatomy of interest or change the bowtie filter that was initially selected.

In this way, by providing a visualization of a representation of the attenuation map of a bowtie filter overlaid with an image obtained from a prior scan, positioning of a subject for a diagnostic scan may be improved. By positioning a subject relative to a bowtie filter such that attenuated beam does not reach the anatomy of interest, image quality may be improved. The technical effect of prompting an operator to align or change the bowtie filter in response to the subject being off-centered relative to the bowtie filter is that repositioning of the subject may be carried out by the operator in accordance with the prompts to attain a well aligned system. In this way, the bowtie filter only significantly attenuates beams not directed toward a skin surface of the patient. Overall, by accurately positioning the subject on the bed relative to the bowtie filter, a scan field of view may remain outside the attenuation region of the filter, thereby improving scan quality.

FIG. 1 illustrates an exemplary CT imaging system 100 configured to allow fast and iterative image reconstruction. Particularly, the CT imaging system 100 is configured to image a subject 112 such as a patient, an inanimate object, one or more manufactured parts, and/or foreign objects such as dental implants, stents, and/or contrast agents present within the body placed on a movable table 115. In one embodiment, the CT imaging system 100 includes a gantry 102, which in turn, may further include at least one x-ray radiation source 104 configured to project a beam of x-ray radiation for use in imaging the subject 112. The x-ray radiation source 104 includes an x-ray tube and a target. The x-ray tube generates x-rays by accelerating and focusing a high-energy beam of electrons onto a rotating target. As individual electrons strike the target, the energy released by interacting with the atoms of the target produces x-ray photons isotropically under a polychromatic spectrum, a maximum energy of the x-ray photons matching that of the incident electrons. The x-ray photons leave the tube through a window that defines an x-ray beam. The beam can then be collimated and conditioned using collimator blades and filter(s).

Specifically, the radiation source 104 is configured to project the x-rays towards a detector array 108 positioned on the opposite side of the gantry 102. Although FIG. 1 depicts only a single radiation source 104, in certain embodiments, multiple radiation sources may be employed to project a plurality of x-rays for acquiring projection data corresponding to the subject 112 at different energy levels. The radiation source may include an x-ray target manufactured of graphite and metal. One or more cameras may be counted on the gantry 102 to capture images of the subject 112 during or prior to a diagnostic scan.

In certain embodiments, the CT imaging system 100 further includes an image processing unit 110 configured to reconstruct images of a target volume of the subject 112 using an iterative or analytic image reconstruction method. For example, the image processing unit 110 may use an analytic image reconstruction approach such as filtered back projection (FBP) to reconstruct images of a target volume of the subject 112. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

FIG. 2 illustrates an exemplary imaging system 200 similar to the CT imaging system 100 of FIG. 1. In accordance with aspects of the present disclosure, the system 200 is configured to perform automatic exposure control responsive to user input. In one embodiment, the system 200 includes the detector array 108 (see FIG. 1). The detector array 108 further includes a plurality of detector elements 202 that together sense the x-ray beam 106 that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

Figure 3:
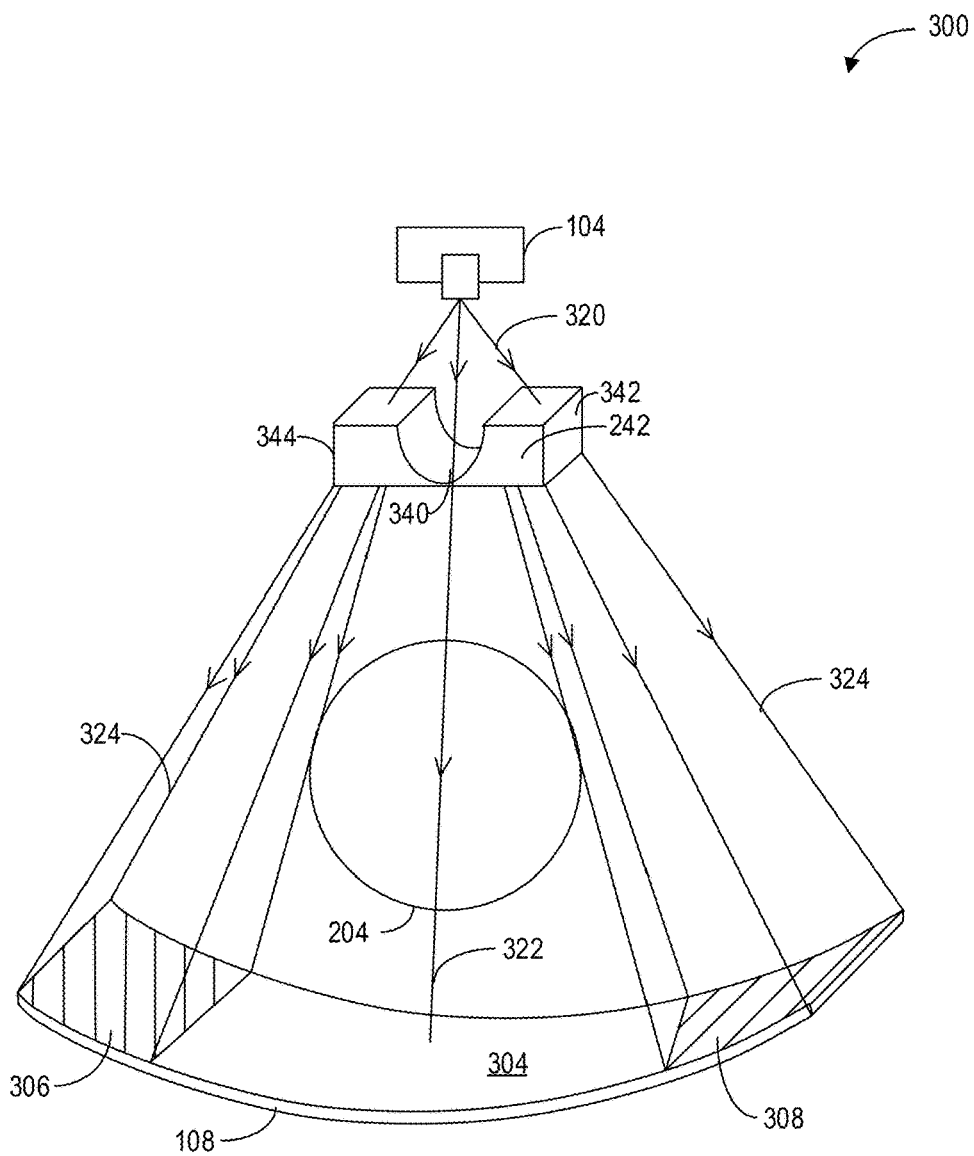
FIG. 3 shows an isometric view of an example bowtie filter used for attenuation of an x-ray beam.

A filter carriage 240 may be mounted within gantry 102 between radiation source 104 and the subject 204. The carriage 240 may travel in and out of the beam in the z-direction while the beam is substantially in the y-direction. A bowtie filter 242 may be housed within a slot formed in a cavity of the carriage. The bowtie filter 242 shown here in rectangular shape as an example. The bowtie filter 242 may alternatively have different shapes and material constructions to provide proper x-ray special spectrum for imaging various types of anatomies. The bowtie filter 242 may change the spatial distribution of the radiation beam in the axial plane of the imaging subject (such as a patient). For example, the re-distributed radiation beam may have higher energy at the center and lower energy at the periphery of the subject. FIG. 3 shows an example attenuation of x-ray beam while passing through a bowtie filter and a subject. Each of the bowtie filters may be designed to image a specific anatomy or section of the human body, such as head, chest, and abdomen. During imaging, one of the bowtie filters may be selected based on the anatomy of the subject to be scanned, and the selected filter may be placed into the radiation beam path. Responsive to a change in the anatomy, the filter may be changed from one to another. Since a bowtie filter causes a gradual attenuation of x-ray beam with lower attenuation at the center of the filter and higher attenuation towards the edges of the filter, it is desired to align the center of the subject 204 with the center of the bowtie filter such that the beam passing through the subject 204 is not attenuated. A visualization of a representation of the attenuation map for a bowtie filter overlaid on an image of an anatomy of interest may be provided to a technician and during conditions when the anatomy of interest is off-centered relative to the bowtie filter, the technician may be prompted to realign the subject. An example method for positioning a subject for a diagnostic scan based on a representation of the attenuation map of a bowtie filter selected for the diagnostic scan is elaborated with reference to FIG. 7.

In certain embodiments, the system 200 is configured to traverse different angular positions around the subject 204 for acquiring desired projection data. Accordingly, the gantry 102 and the components mounted thereon (such as the radiation source 104, the filter housing 240, and the detector 202) may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table motor 228 and table 115. Particularly, the table motor controller 226 controls the table motor 228 to move the table 115 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and the image reconstructor 230 may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

In this way, FIGS. 1-2 provide for an imaging system, comprising a gantry for receiving an imaging subject, a radiation source positioned in the gantry for emitting radiation exposure, an attenuation filter positioned between the radiation source and an imaging subject, a computation device with instructions stored in a non-transient memory to: prior to a diagnostic scan of an anatomical feature of the imaging subject, provide visualization, via the display device, of an overlay of a representation of the attenuation map displaying a degree of attenuation of a radiation beam passing through the attenuation filter and an image of the anatomical feature of the imaging subject, and send out a notification to an operator in response to the image being off-centered relative to a center of the attenuation filter.

FIG. 3 shows an isometric view 300 of an example bowtie filter 242 used for attenuation of an x-ray beam. X-ray from an x-ray source 104 may pass through a subject 204 being scanned before reaching a detector array 304. The attenuation of the x-ray beam while passing through the subject, as identified by image processing the data captured at the detector array 304, may provide information about the structural details (such as anatomy) of the subject. An attenuation system such as a bowtie filter 242 may be placed between the x-ray source 1-4 and the subject 204 to attenuate some of the radiations passing through the filter 242.

The filter 242 may include a central portion 340 that has lower thickness compared to the two edges 342 and 344. In this example, the central portion may have a curved surface (facing the beam) while the edges may have flat surfaces (facing the beam). The attenuation capability of the bowtie filter 242 is lowest at the central portion 340 and highest at the two edges 342 and 344. In one example, the bowtie filter may be coated with an attenuating material with the thickness of the coating being higher towards the edges relative to the central portion.

In one example, attenuation of the beam may start from region on the bowtie filter 242, the region also referred to as attenuation boundary and extend to the edges of the filter. X-ray beam passing through the portion of the filter between the attenuation boundary and one of the edges of the filter is attenuated with the degree of attenuation increasing from the boundary to the edges. Attenuation of x-ray beam passing through the portion of the filter between the attenuation boundary and the center of the filter is lower than that outside the boundary. In this way, the degree of attenuation of x-ray beam passing through the bowtie filter 242 increases between the central portion 340 and each of the edges 342 and 344. The attenuation boundary and the gradual change in attenuation changes based on the size of the bowtie filter.

The x-ray beam 320 emitted from the x-ray source may pass through different regions of the bowtie filter 242. The central beam 322 passing through the central portion 340 may then pass through the subject 204 before being incident on the central portion 304 of the detector array 108. Attenuation of the central beam 322 at the bowtie filter 242 may be low to none. However, this central beam 322 may be attenuated at the subject 204 before reaching the detector array 108. Peripheral x-ray beams 324 which may not pass through the subject 204 may be attenuated to a higher degree (relative to the attenuation of the central beam 322) by the bowtie filter 242 before reaching the peripheral regions 306 and 308 on the detector array 108. In this way, by attenuating the portion of the x-ray beam that does not significantly pass through the subject 204 the flux of x-ray beam reaching the detector may be uniform throughout the detector array and one or more discreet detector element is not overexposed.

During a scan, if the subject is not centered or aligned with the center of the bowtie filter, the x-ray beam reaching the subject may have passed through regions of the bowtie filter that are between the attenuation boundary and edges of the filter, thereby causing a attenuated beam to pass through the subject. Passing of an attenuated beam through the subject may result in inferior image quality.

Figure 7:
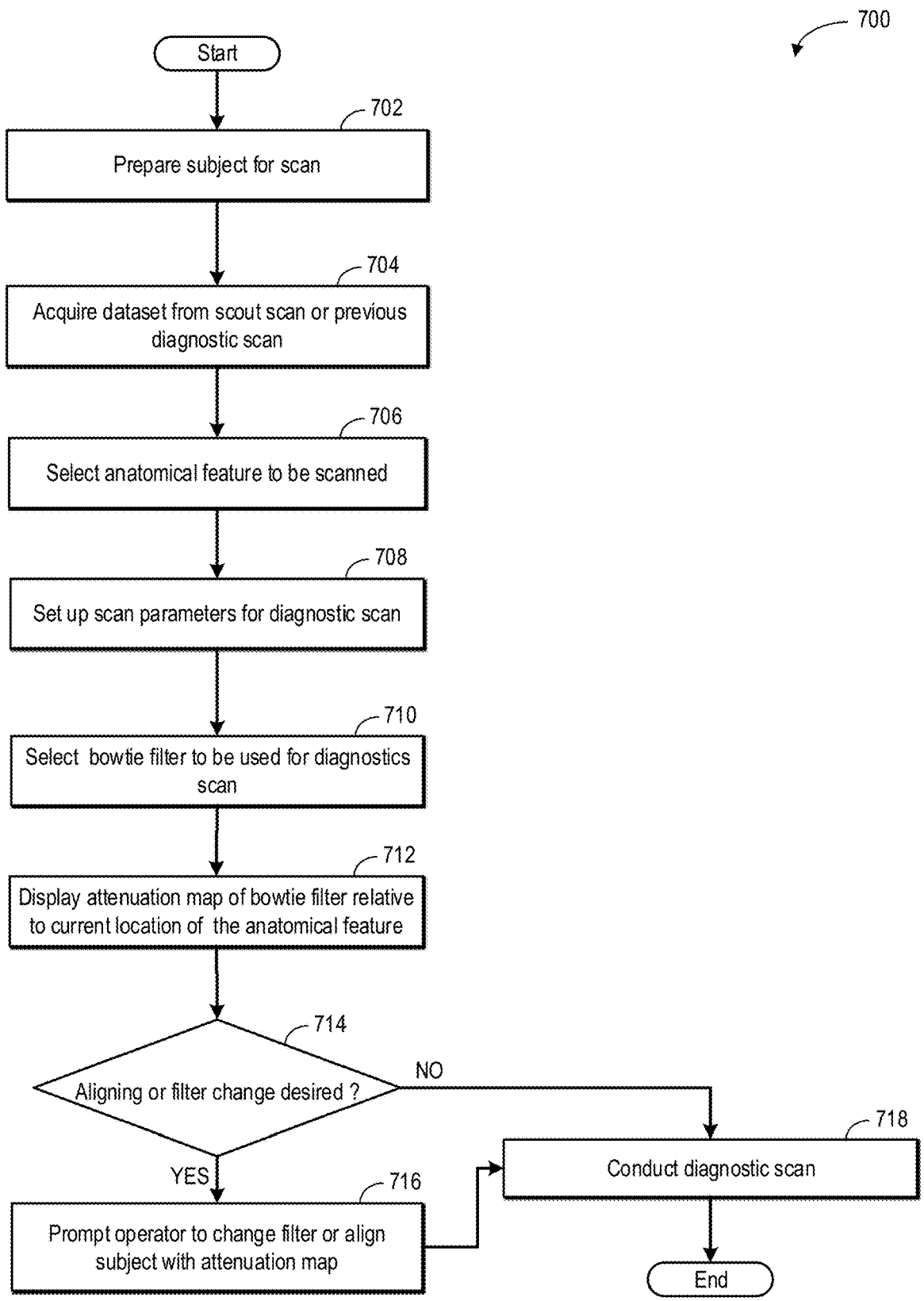
FIG. 7 shows a flow chart of an example method for positioning a subject for a diagnostic scan based on a representation of the attenuation map of a bowtie filter selected for the diagnostic scan.

FIG. 7 shows an example method 700 for positioning a subject for a diagnostic scan based on a representation of the attenuation map of an attenuation system (such as bowtie filter 242 in FIGS. 2-3) selected for the diagnostic scan. Method 600 and all methods described herein may be performed according to instructions stored in the non-transitory memory in a computing device (such as computer 216 of FIG. 2) of the imaging system.

At 702, a subject (such as a patient) may be prepared for a diagnostic scan. One or more anatomies of the subject (such as body parts or systems including brain, heart, respiratory system, etc.) may be identified to be of interest (to be scanned). Prior to a diagnostic scan, a scout scan may be carried out. A scout scan provides a projection view along a longitudinal axis of the imaging subject and generally provides aggregations each including internal structures of the subject. A scout scan may be used to identify the region of interest of the subject for the subsequent diagnostic scan.

Scan parameters may be set up for carrying out a scout scan. For example, an operator may input or select the scan parameters according to a scanning protocol or a menu. Scan parameters may include setting scan timing. As one example, the scan timing may include a start time and a duration for imaging each section. The subject (such as subject 204 in FIG. 2) of the imaging scans may be positioned on a motorized table (such as table 115 in FIG. 2). A table motor controller 226 may control a table motor 228 to move the table 115 so that a desired anatomy of the subject is within the gantry for imaging.

As an example, a series of diagnostic scans may be carried out for a desired anatomy. Scan parameters for the first scan in the series of diagnostic scans may be set up for carrying out a diagnostic scan. An operator may input or select the scan parameters according to a scanning protocol or a menu.

At 704, a scout scan or a first diagnostic scan of the subject may be carried out. Method 700 may start acquiring the dataset of the imaging subject and simultaneously monitor the anatomy of the imaging subject. For example, the radiation source (such as 104 of FIGS. 1-2) may be activated, and radiation exposure (such as 106 of FIG. 2) of the imaging subject may be started.

The dataset is acquired from the detector (such as 108 of FIG. 2) upon receiving the transmitted radiation signal from the imaging subject. As one example, the anatomy of the imaging subject may be monitored by analyzing the acquired dataset. As another example, the anatomy of the imaging subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, type such as the head, the chest, and the abdomen. Dataset acquired from different sections of the subject may be re-constructed to form an image or a series of images and the image(s) may be saved in the memory of the imaging device.

Based on the data acquired during the scout scan and/or a first scan in a series of diagnostic scans, at 706, an anatomical feature of the subject that is to be subsequently scanned may be selected. An image of the selected anatomical feature of interest, as obtained from the scout scan data or the first diagnostic scan data, may be retrieved. This image may show the current location of the anatomical feature with respect to the scanning apparatus.

At 708, without further moving the subject, scan parameters may be setup for the subsequent diagnostic scan of the selected anatomical feature of interest. An operator may input or select the scan parameters according to a scanning protocol or a menu for the diagnostic scan. The parameters may include setting scan timing such as a start time and a duration for imaging each section. Anatomy information of the imaging subject may be loaded to the memory of the computation device. The anatomy information may be acquired from a pre-scan. The anatomy information may be acquired from the prior scout scan or a localized scan. This step may also include moving the imaging subject via the motorized table so that the proper section of the subject is within the gantry for imaging.

At 710, a bowtie filter corresponding to the anatomy of interest to be scanned may be selected. The size of the filter may be chosen based on the anatomy of imaging subject that is to be imaged. As an example, a larger bowtie filter may be selected if a larger anatomy is to be scanned and a smaller bowtie filter may be selected if a smaller anatomy is to be scanned. In one example, the smaller bowtie filter may have a smaller central portion relative to the edges compared to a larger bowtie filter. A bowtie filter may be positioned in the path of the x-ray beam by operating a motor coupled to a carriage including the bowtie filter. A bowtie filter is used to shape an x-ray beam and equalize its flux reaching different detector channels. Bowtie filters are commonly employed in CT scanners to minimize radiation dose by reducing in tensity variations across detector elements in the presence of patient anatomy.

At 712, a representation of the attenuation map of the bowtie filter may be displayed relative to a current location of the anatomical feature. A representation of the attenuation map shows a degree of attenuation of the x-ray beam reaching the scan field of view (SFOV) of the anatomical feature of interest. In one example, for each bowtie filter, a representation of the attenuation map may be calibrated and stored in the memory of the scanning device. The representation of the attenuation map may also depend on the distance between the subject and the bowtie filter. The controller may determine the size and characteristics (such as width of central portion and edges) of the selected bowtie filter and a sensed position of the bowtie filter relative to the subject such as the distance between the subject (at its current location) and the bowtie filter. The controller may then use a look up table to determine the representation of the attenuation map of the bowtie filter relative to the current location of the anatomical feature with the size, characteristics of the bowtie filter and the distance as inputs and the representation of the attenuation map as output. The representation of the attenuation map showing the degree of attenuation of the x-ray beam upon passing through the bowtie filter is overlaid on the image of the anatomical feature of interest.

A visualization of the overlay of the representation of the attenuation map with the SFOV of the anatomical feature of interest may be provided to the operator. The operator may select when the overlay may be displayed on the image of the anatomical feature. In one example, a colored representation of the attenuation map may be overlaid with a grayscale image of the anatomical feature and displayed on a monitor visible to the operator. The gradation of attenuation (degree of attenuation) may be shown as a change in color gradient as the attenuation increases from the attenuation boundary to the edge of the SFOV. Two or more colors may be used to visually depict the representation of the attenuation map relative to the image. The attenuation boundary at which beam attenuation starts may be displayed on the image.

In another example, one or more cameras coupled to the gantry may capture an image of the subject and the representation of the attenuation map may be displayed overlaid on the image captured by the camera. The image captured by the camera may externally show the anatomy of interest. As an example, if a section of the brain is to be scanned, the camera map capture an image of the head of the patient and overlay the image with the representation of the attenuation map to show the operator the regions on the head which are likely to receive attenuated beam.

In yet another example, the representation of the attenuation map and the attenuation boundary may be available in augmented reality such as the boundary and the map overlaid with an image of the anatomy may be visible to the operator if the operator wears a specific kind of glasses. In a further example, a laser beam or a light beam may be projected directly on the patient to show the attenuation boundary. As an example, if a section of the brain is to be scanned, a laser beam may be projected on a portion of the patient's head denoting the attenuation boundary of the bowtie filter used.

Different sizes of bowtie filters may be color coded such that a particular size of the filter may correspond to a distinct color. In this way, the color of the representation of the attenuation map as visible to the operator may provide an identification of the size of the bowtie filter used.

FIG. 4A shows a first example positioning of a patient shown in a scout scan image relative to a representation of the attenuation map corresponding to a selected bowtie filter. The image 404 of the anatomy of interest may be retrieved from a scout scan of the patient acquired at the same position of the patient at which the subsequent diagnostic scan is to be carried out. The representation of the attenuation map of the selected bowtie filter may be retrieved from the memory of the imaging device and overlaid on the scout image 404. The representation of the attenuation map may include a first attenuation boundary 408 and a second attenuation boundary 406 on each side of the image 404. The representation of the attenuation map includes a first attenuation zone 414 and a second attenuation zone 412 on each side of the image 404. In the first attenuation zone, the degree of attenuation of the x-ray beam increases from the first attenuation boundary 408 away from the center of the image. Similarly, in the second attenuation zone, the degree of attenuation of the x-ray beam increases from the second attenuation boundary 406 away from the center of the image 404. In this example, the scan field of view of the image 404 is completely between two attenuation boundaries 406 and 408. Therefore, the x-ray beam used to scan this image is not significantly attenuated via the bowtie filter.

Returning to FIG. 7, at 714, the routine includes determining if aligning of the subject or a change in filter is desired. In one example, based on image processing, the controller may determine if the desired scan field of view is outside the attenuation boundary such that at least a part of the image to be captured during the diagnostic scan may be formed by an attenuated x-ray beam passing through a part of the anatomy of interest. In another example, the controller may determine if the scan field of view of the image overlaps with a portion of the representation of the attenuation map having a higher than threshold degree of attenuation. As an example, the threshold degree of attenuation may be between 2% and 15% of the original flux. If an attenuated beam is used for scanning even a part of the anatomy of interest, the image quality may be adversely affected. In another example, upon visual inspection of the visualization of the overlay between the representation of the attenuation map of the bowtie filter and the anatomical feature (in its current location), the operator may determine if a change in alignment and/or a change in filter may be desired for improved imaging quality.

Further, if the size of the bowtie filter selected for the diagnostic scan is smaller than optimal, the attenuation boundary of the bowtie filter may be within the scan field of view (SFOV) of the image. Therefore, image processing of the overlay may be carried out to determine if the attenuation boundary of the bowtie filter overlaps with the SFOV of the anatomy of interest.

FIG. 4B shows a second example 450 positioning of a patient shown in a scout scan image relative to a representation of the attenuation map corresponding to a selected bowtie filter. The image 405 of the anatomy of interest may be retrieved from a scout scan of the patient acquired at the same position of the patient at which the subsequent diagnostic scan is to be carried out. The representation of the attenuation map of the selected bowtie filter may be retrieved from the memory of the imaging device and overlaid on the scout image 405. The representation of the attenuation map may include a first attenuation boundary 408 and a second attenuation boundary 406 on each side of the image 405. In this example, the scan field of view (SFOV) of the image 405 is not completely between two attenuation boundaries 406 and 408 and the SFOV is seen overlapping with the second attenuation zone 412. During such a condition, it may be desired to shift the patient in a way to position the SFOV within the two attenuation boundaries 406 and 408 prior to the diagnostic scan.

FIG. 4C shows a third example positioning of a patient shown in a scout scan image relative to a representation of the attenuation map corresponding to a selected bowtie filter. The image 407 of the anatomy of interest may be retrieved from a scout scan of the patient acquired at the same position of the patient at which the subsequent diagnostic scan is to be carried out. In this example, it is seen that the due to a tilt in the position of the head of the patient, the SFOV of the image 407 is not completely between two attenuation boundaries 406 and 408 and the SFOV is seen overlapping with the second attenuation zone 412. During such a condition, it may be desired to shift the patient in a way (such as correct the tilt of the head) to position the SFOV within the two attenuation boundaries 406 and 408 prior to the diagnostic scan.

FIG. 5A shows a first example 500 of positioning of a bowtie filter attenuation region relative to a current position to an anatomical feature. The image 502 of the anatomy of interest may be retrieved from a diagnostic scan of the patient acquired at the same position of the patient at which the subsequent diagnostic scan is to be carried out. As an example, when a series of diagnostic scans are being carried out, a first image obtained of the anatomy may be used to align the patient for subsequent diagnostic scans. The representation of the attenuation map of the selected bowtie filter may be retrieved from the memory of the imaging device and overlaid on the image 502. The boundary 504 of the attenuation map is shown overlaid with the image 502. The attenuation of x-ray beams reaching the part of the image outside the attenuation boundary may increase gradually away from the center of the image 502. In this example, it is observed that the SFOV of the anatomy of interest is within the attenuation boundary. From this overlay it may be inferred that the x-ray beam used for imaging of the anatomy as seen in this example was not substantially attenuated and therefore further alignment of the patient may not be desired.

FIG. 5B shows a second example 550 of positioning of a bowtie filter attenuation region relative to a current position to an anatomical feature. The image 503 of the anatomy of interest may be retrieved from a diagnostic scan of the patient acquired at the same position of the patient at which the subsequent diagnostic scan is to be carried out. The representation of the attenuation map of the selected bowtie filter may be retrieved from the memory of the imaging device and overlaid on the image 503. The boundary 505 of the representation of the attenuation map is shown overlaid with the image 503. The attenuation of x-ray beams reaching the part of the image outside the attenuation boundary may increase gradually away from the center of the image 503. In this example, it is observed that a portion 506 of the SFOV of the anatomy of interest is outside the attenuation boundary. From this overlay it may be inferred that the x-ray beam used for imaging of a portion of the anatomy as seen in this example was attenuated. During such a condition, it may be desired to shift the patient in a way to position the SFOV entirely within the boundary 505 of the representation of the attenuation map prior to the subsequent diagnostic scan.

FIG. 6A shows a first example 600 of an attenuation region of a first bowtie filter relative to a current position of an anatomical feature. The image 602 of the anatomy of interest may be retrieved from a diagnostic scan of the patient acquired at the same position of the patient at which the subsequent diagnostic scan is to be carried out. As an example, when a series of diagnostic scans are being carried out, a first image obtained of the anatomy may be used to align the patient for subsequent diagnostic scans. The representation of the attenuation map of the selected bowtie filter may be retrieved from the memory of the imaging device and overlaid on the image 602. The boundary 604 of the representation of the attenuation map is shown overlaid with the image 502. The attenuation of x-ray beam reaching the part of the image outside the attenuation boundary may increase gradually away from the center of the image 602. In this example, it is observed that the SFOV of the anatomy of interest in completely within the attenuation boundary. From this overlay it may be inferred that the x-ray beam used for imaging of the anatomy as seen in this example was not substantially attenuated and therefore a change in the bowtie filter size may not be desired. The subsequent diagnostic scan may be carried out with the first bowtie filter.

FIG. 6B shows a second example 650 of an attenuation region of a second bowtie filter relative to a current position to an anatomical feature. The image 603 of the anatomy of interest may be retrieved from a diagnostic scan of the patient acquired at the same position of the patient at which the subsequent diagnostic scan is to be carried out. The representation of the attenuation map of the selected bowtie filter may be retrieved from the memory of the imaging device and overlaid on the image 603. The boundary 606 of the representation of the attenuation map is shown overlaid with the image 603. The attenuation of x-ray beams reaching the part of the image outside the attenuation boundary may increase gradually away from the center of the image 603.

In this example, it is observed that the attenuation boundary 606 is enclosed within the SFOV of the anatomy of interest and a portion 605 of the SFOV is outside the attenuation boundary. From this overlay it may be inferred that the x-ray beam used for imaging of the peripheral portion of the anatomy as seen in this example was attenuated. The second bowtie filter selected for the diagnostic scan may be too small to provide substantially un-attenuated beam to the entire anatomy of interest. During such a condition, it may be desired to change the bowtie filter to a larger filter such that the attenuation boundary is outside the SFOV.

Returning to FIG. 7, if it is determined at 714 that aligning of the subject or a change in filter is desired, at 716, the operator may be prompted to change the filter or align the subject relative to the attenuation of the current bowtie filter. In one example, the prompt may be in the form of a message on a display device available to the operator to adjust a position of the subject to be scanned. Adjusting the position of the subject includes shifting the subject and/or a bed on which the subject is being positioned to align a center of the anatomy of interest with a center of the bowtie filter. As an example, to align the subject, the subject may be physically shifted on the bed or a height of the bed may be increased/decreased. The prompt may also include a suggested amount of shifting of the patient and/or a bed needed to align the center of the anatomy with the center of the bowtie filter. In one example, the prompt may provide a visualization of a desired subject outline that is centered with reference to the bowtie filter and the operator may shift the patient or move the bed to position the subject on the provided outline. The prompt may also include a suggestion of a different filter that may be effectively used during the subsequent scan.

In an alternate embodiment, the prompting may not be provided and the operator may make a determination of the adjustment. The adjustment may include shifting a position of the patient and/or a bed needed to align the center of the anatomy with the center of the bowtie filter based on the visualization of the overlap of the representation of the attenuation map with the SFOV of the anatomy of interest. The operator may also determine a different bowtie filter to be used for the subsequent scan.

In addition to the alignment of the subject with reference to the center of the bowtie filter, other centering tool for subject positioning may be used separately or in combination. Other centering tools including lasers, cameras, scout scans, etc. may be used for alignment of the subject with reference to the center of the bowtie filter.

Once the alignment of the subject with reference to the bowtie filter is completed and/or the bowtie filter has been changed, at 718, the subsequent diagnostic scan may be carried out and data may be collected. If at step 714 it is determined that the aligning of the subject or a change in filter is not desired, the routine may directly proceed to 718 to carry out the diagnostic scan without any change to the position of the subject or the bowtie filter.

In this way, prior to a diagnostic scan of an anatomy of a patient, a selection of a bowtie filter to be positioned between a radiation source and the patient may be received; a representation of the attenuation map for the bowtie filter showing a variation in a degree of attenuation of a radiation passing through the bowtie filter may be retrieved; the representation of the attenuation map may be overlaid with an image of the anatomy captured at a current location of the patient; and in response to a field of view of the image overlapping with a portion of the representation of the attenuation map having a higher than threshold degree of attenuation, an operator may be prompted to adjust a position of the patient.

In one example, a method for an imaging system, comprises: displaying a representation of the attenuation map of a filter relative to a current location of an anatomical feature of a subject; and in response to the anatomical feature being within a region of the representation of the attenuation map, prompting an operator to reposition the subject. In the preceding example, additionally or optionally, the filter is a bowtie filer positioned in a path of an x-ray beam between a source of the x-ray beam and the subject to be scanned. In any or all of the preceding examples, additionally or optionally, the representation of the attenuation map includes a degree of attenuation of a portion of the x-ray beam passing through the filter, the degree of attenuation displayed as a color gradient. In any or all of the preceding examples, additionally or optionally, the degree of attenuation gradually increases from an attenuation boundary on the representation of the attenuation map away from a center of the filter. In any or all of the preceding examples, additionally or optionally, the region of the representation of the attenuation map includes a portion of the representation of the attenuation map outside the attenuation boundary away from the center of the filter. In any or all of the preceding examples, additionally or optionally, the displaying includes overlaying the representation of the attenuation map on an image of the anatomical feature captured at the current location. In any or all of the preceding examples, the method further comprising, additionally or optionally, prompting the operator to change the filter in response to the attenuation boundary completely overlapping with a scan field of view of the image. In any or all of the preceding examples, additionally or optionally, the anatomical feature being within the region includes the scan field of view of the image being at least partially within the region of the representation of the attenuation map. In any or all of the preceding examples, additionally or optionally, the image is obtained from a scout scan performed on the subject. In any or all of the preceding examples, additionally or optionally, the image is obtained from a first diagnostic scan in a series of diagnostic scans performed on the subject. In any or all of the preceding examples, additionally or optionally, the displaying the representation of the attenuation map includes displaying an overlay of the representation of the attenuation map and the image of the anatomical feature to the operator via a display device. In any or all of the preceding examples, additionally or optionally, the displaying the representation of the attenuation map includes projecting the attenuation boundary on to another image of the subject captured via one or more cameras mounted on the imaging system, the another image visible to the operator. In any or all of the preceding examples, additionally or optionally, repositioning the subject includes aligning a center of the anatomical feature with the center of the filter by shifting the subject and/or a bed on which the subject is being positioned.

Another example method for an imaging device comprises: prior to a diagnostic scan of an anatomy of a patient, receiving a selection of a bowtie filter to be positioned between a radiation source and the patient, retrieving a representation of the attenuation map for the bowtie filter showing a variation in a degree of attenuation of a radiation passing through the bowtie filter, overlaying the representation of the attenuation map with an image of the anatomy captured at a current location of the patient, and in response to a field of view of the image overlapping with a portion of the representation of the attenuation map having a higher than threshold degree of attenuation, prompting an operator to adjust a position of the patient. In any or all of the preceding examples, additionally or optionally, the image of the anatomy is obtained from one of a scout scan and another diagnostic scan performed on the patient immediately prior to the diagnostic scan. In any or all of the preceding examples, additionally or optionally, the overlaying of the representation of the attenuation map with the image is visually displayed to the operator via a screen. In any or all of the preceding examples, additionally or optionally, adjusting the position of the patient includes shifting the patient and/or a bed on which the patient is being positioned to align a center of the anatomy with a center of the bowtie filter. In any or all of the preceding examples, additionally or optionally, the prompting includes indicating an amount of shifting of the patient and/or a bed needed to align the center of the anatomy with the center of the bowtie filter.

In yet another example, an imaging system, comprises: a gantry for receiving an imaging subject, a radiation source positioned in the gantry for emitting radiation exposure, an attenuation filter positioned between the radiation source and an imaging subject, a computation device with instructions stored in a non-transient memory to: prior to a diagnostic scan of an anatomical feature of the imaging subject, provide visualization, via the display device, of an overlay of an attenuation map displaying a degree of attenuation of a radiation beam passing through the attenuation filter and an image of the anatomical feature of the imaging subject; and send out a notification to an operator in response to the image being off-centered relative to a center of the attenuation filter. In the preceding example, additionally or optionally, the image of the anatomical feature is obtained from a scout scan and/or another diagnostic scan of the anatomical feature of the imaging subject carried out immediately prior to the diagnostic scan with the imaging subject being at a current position.

FIGS. 1-3 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
displaying a representation of an attenuation map of a filter relative to a current location of an anatomical feature of a subject; and in response to the anatomical feature being within a region of the representation of the attenuation map, prompting an operator to reposition the subject, wherein the representation of the attenuation map includes a degree of attenuation of a portion of an x-ray beam passing through the filter, the degree of attenuation displayed as a color gradient.

2. The method of claim 1, wherein the filter is a bowtie filer positioned in a path of the x-ray beam between a source of the x-ray beam and the subject to be scanned.

3. The method of claim 2, wherein the degree of attenuation gradually increases from an attenuation boundary on the representation of the attenuation map away from a center of the filter.

4. The method of claim 3, wherein the region of the representation of the attenuation map includes a portion of the representation of the attenuation map outside the attenuation boundary away from the center of the filter.

5. The method of claim 3, wherein the displaying the representation of the attenuation map includes projecting the attenuation boundary on to another image of the subject captured via one or more cameras mounted on the imaging system, the another image visible to the operator.

6. The method of claim 3, wherein repositioning the subject includes aligning a center of the anatomical feature with the center of the filter by shifting the subject and/or a bed on which the subject is being positioned.

7. The method of claim 3, wherein the displaying includes overlaying the representation of the attenuation map on an image of the anatomical feature captured at the current location.

8. The method of claim 7, wherein the image is obtained from a scout scan performed on the subject.

9. The method of claim 7, wherein the image is obtained from a first diagnostic scan in a series of diagnostic scans performed on the subject.

10. The method of claim 7, wherein the displaying the representation of the attenuation map includes displaying an overlay of the representation of the attenuation map and the image of the anatomical feature to the operator via a display device.

11. The method of claim 10, further comprising, prompting the operator to change the filter in response to the attenuation boundary completely overlapping with a scan field of view of the image.

12. The method of claim 11, wherein the anatomical feature being within the region includes the scan field of view of the image being at least partially within the region of the representation of the attenuation map.

13. A method for an imaging device, comprising:
prior to a diagnostic scan of an anatomy of a patient,
receiving a selection of a bowtie filter to be positioned between a radiation source and the patient;
retrieving a representation of an attenuation map for the bowtie filter showing a variation in a degree of attenuation of a radiation passing through the bowtie filter;
overlaying the representation of the attenuation map with an image of the anatomy captured at a current location of the patient; and
in response to a field of view of the image overlapping with a portion of the representation of the attenuation map having a higher than threshold degree of attenuation,
prompting an operator to adjust a position of the patient.

14. The method of claim 13, further comprising, obtaining the image of the anatomy from one of a scout scan and another diagnostic scan performed on the patient immediately prior to the diagnostic scan.

15. The method of claim 13, wherein the overlaying of the representation of the attenuation map with the image is visually displayed to the operator via a screen.

16. The method of claim 13, wherein adjusting the position of the patient includes shifting the patient and/or a bed on which the patient is being positioned to align a center of the anatomy with a center of the bowtie filter.

17. The method of claim 16, wherein the prompting includes indicating an amount of shifting of the patient and/or a bed needed to align the center of the anatomy with the center of the bowtie filter.

18. An imaging system, comprising:
a gantry for receiving an imaging subject;
a radiation source positioned in the gantry for emitting radiation exposure;
an attenuation filter positioned between the radiation source and the imaging subject;
a computation device with instructions stored in a non-transient memory to:
prior to a diagnostic scan of an anatomical feature of the imaging subject, provide visualization, via a display device, of an overlay of an attenuation map displaying a degree of attenuation of a radiation beam passing through the attenuation filter and an image of the anatomical feature of the imaging subject; and
send out a notification to an operator in response to the image being off-centered relative to a center of the attenuation filter.

19. The system of claim 18, wherein the image of the anatomical feature is obtained from a scout scan and/or another diagnostic scan of the anatomical feature of the imaging subject carried out immediately prior to the diagnostic scan with the imaging subject being at a current position.

\* \* \* \* \*